(12) United States Patent
Ryan et al.

(10) Patent No.: US 9,269,468 B2
(45) Date of Patent: Feb. 23, 2016

(54) X-RAY BEAM CONDITIONING

(71) Applicant: Jordan Valley Semiconductors Ltd., Migdal HaEmek (IL)

(72) Inventors: Paul Anthony Ryan, Darlington (GB); John Leonard Wall, Durham (GB); John Spence, Durham (GB)

(73) Assignee: Jordan Valley Semiconductors Ltd., Migdal HaEmek (IL)

( * ) Notice: Subject to any disclaimer, the term of this patent is extended or adjusted under 35 U.S.C. 154(b) by 282 days.

(21) Appl. No.: 13/872,196

(22) Filed: Apr. 29, 2013

(65) Prior Publication Data

US 2013/0287178 A1    Oct. 31, 2013

Related U.S. Application Data

(60) Provisional application No. 61/640,062, filed on Apr. 30, 2012.

(51) Int. Cl.
*G21K 1/06* (2006.01)
*G01N 23/20* (2006.01)

(52) U.S. Cl.
CPC ........ *G21K 1/06* (2013.01); *G01N 23/20* (2013.01); *G01N 2223/308* (2013.01); *G01N 2223/315* (2013.01); *G01N 2223/316* (2013.01)

(58) Field of Classification Search
CPC ......... G21K 1/06; G21K 1/062; G01N 23/20; G01N 23/20008; G01N 23/20016; G01N 23/20091; G01N 23/205; G01N 23/2055; G01N 23/207; G01N 2223/05; G01N 2223/056; G01N 2223/0561; G01N 2223/315

USPC ................ 378/70–73, 75, 76, 82, 84, 85, 145
See application file for complete search history.

(56) References Cited

U.S. PATENT DOCUMENTS

| | | | | |
|---|---|---|---|---|
| 4,567,605 A * | 1/1986 | Bartels | .......................... | 378/85 |
| 4,821,301 A * | 4/1989 | Cocks et al. | .................... | 378/70 |
| 5,016,267 A * | 5/1991 | Wilkins | .................... | G21K 1/00 250/370.05 |
| 5,199,058 A * | 3/1993 | Tani | ........................ | G21K 1/06 378/82 |
| 5,245,648 A * | 9/1993 | Kinney | ................ | G01N 23/046 378/145 |
| 5,509,043 A * | 4/1996 | Van Der Sluis | ................. | 378/85 |
| 5,802,137 A * | 9/1998 | Wilkins | ........................ | 378/85 |

(Continued)

FOREIGN PATENT DOCUMENTS

JP    09-49811    *    2/1997    ........... G01N 23/207

OTHER PUBLICATIONS

M. Schuster and H. Göbel, "Parallel-beam coupling into channel-cut monochromators using curved graded multilayers," J. Phys. D: Appl. Phys. 28 (1995) A270-A275.*

(Continued)

*Primary Examiner* — Allen C. Ho
(74) *Attorney, Agent, or Firm* — D.Kligler Services Ltd.

(57) ABSTRACT

An X-ray optical device includes a crystal containing a channel, which passes through the crystal and has multiple internal faces. A mount is configured to hold the crystal in a fixed location relative to a source of an X-ray beam and to shift the crystal automatically between two predefined dispositions: a first disposition in which the X-ray beam passes through the channel while diffracting from one or more of the internal faces, and a second disposition in which the X-ray beam passes through the channel without diffraction by the crystal.

9 Claims, 4 Drawing Sheets

(56) References Cited

U.S. PATENT DOCUMENTS

| | | | | |
|---|---|---|---|---|
| 6,226,349 | B1* | 5/2001 | Schuster et al. | 378/84 |
| 6,385,289 | B1* | 5/2002 | Kikuchi | G01N 23/20 378/70 |
| 6,574,306 | B2* | 6/2003 | Kikuchi | 378/84 |
| 6,665,372 | B2 | 12/2003 | Bahr et al. | |
| 7,035,373 | B2* | 4/2006 | Omote | 378/79 |
| 7,120,228 | B2 | 10/2006 | Yokhin et al. | |
| 7,257,192 | B2* | 8/2007 | Omote | 378/70 |
| 7,542,548 | B2* | 6/2009 | Matsuo et al. | 378/84 |
| 7,551,719 | B2 | 6/2009 | Yokhin et al. | |
| 7,646,849 | B2* | 1/2010 | Iwasaki | B82Y 10/00 378/70 |
| 7,684,543 | B2* | 3/2010 | Matsuo et al. | 378/85 |
| 7,711,091 | B2 | 5/2010 | Sasaki et al. | |
| 7,801,272 | B2* | 9/2010 | Toraya | 378/71 |
| 7,817,779 | B2* | 10/2010 | Ando | 378/71 |
| 8,085,900 | B2* | 12/2011 | Omote | 378/84 |
| 8,249,220 | B2* | 8/2012 | Verman et al. | 378/147 |
| 8,340,248 | B2* | 12/2012 | Toraya et al. | 378/70 |
| 8,422,633 | B2* | 4/2013 | Lantz et al. | 378/84 |

OTHER PUBLICATIONS

Loxley et al., "The Performance of Channel Cut Collimators for Precision X-Ray Diffraction Studies of Epitaxial Layers", MRS Proceedings, vol. 208, pp. 107-112, 1991.

Bartels, W. J., "Characterization of thin layers on perfect crystals with a multipurpose high resolution x-ray diffractometer", Journal of Vacuum Science and Technology B1, vol. 1, issue 2, pp. 338-345, Apr. 1983.

Jordan Valley Semiconductors Ltd., "D1 Evolution System", 2 pages, Israel, year 2013.

Crystal Scientific, "Channel Cut Crystals", UK, 1 page, year 2011.

AXO Dresden GMBH, "Multilayer mirrors—potentials for imaging, monochromating, collimating or focusing optics", ACTOP 11, Oxford, UK, Apr. 4-5, 2011.

* cited by examiner

X-RAY BEAM CONDITIONING

CROSS-REFERENCE TO RELATED APPLICATIONS

This application claims the benefit of U.S. Provisional Patent Application 61/640,062, filed Apr. 30, 2012, which is incorporated herein by reference.

FIELD OF THE INVENTION

The present invention relates generally to X-ray systems, and particularly to devices and methods for controlling the properties of an X-ray beam.

BACKGROUND

Various techniques for X-ray analysis are known in the art, such as measurement of X-ray diffraction, reflectivity, fluorescence, or other types of scattering from a sample. Typically, each type of measurement requires an X-ray beam with certain qualities, such as collimation (i.e., angular spread of the beam), monochromatization (range of photon energies), and focal size (beam width on the sample). In general, the desired qualities may vary depending on the type of sample and objectives of the measurement. The beams that are output directly by common X-ray sources, however, such as metal-anode X-ray tubes, for the most part do not meet these quality constraints.

To overcome these limitations, X-ray optical elements have been developed to enhance beam collimation, monochromatization and focal properties. For example, a variety of X-ray mirrors are commercially available to collect and then collimate and/or focus an X-ray beam, such as multi-layer mirrors made by AXO DRESDEN GmbH (Dresden, Germany) and Rigaku Corporation (Tokyo, Japan). As another example, to achieve particularly fine collimation and monochromaticity, the X-ray beam may be reflected through a channel in a crystal of highly-perfect silicon or germanium, such as channel-cut crystals manufactured by Crystal Scientific (UK) Ltd. (Alnwick, Northumberland, UK).

Some X-ray measurement systems are designed to accommodate adjustable and/or interchangeable optics, to enable the user to vary or select beam properties to suit different types of measurements. This sort of capability is available in certain commercially-available systems, such as the D1 Evolution system produced by Jordan Valley Semiconductors Ltd. (Migdal Ha'emek, Israel). Multifunction systems of this sort are described in the patent literature, for example, in U.S. Pat. Nos. 7,120,228 and 7,551,719, whose disclosures are incorporated herein by reference. X-ray diffractometers with interchangeable optical features are also described, for example, in U.S. Pat. Nos. 6,665,372, 7,711,091 and 7,684,543.

SUMMARY

Embodiments of the present invention that are described hereinbelow provide improved devices and methods for automated control of X-ray beam properties.

There is therefore provided, in accordance with an embodiment of the present invention, an X-ray optical device, which includes a crystal containing a channel, which passes through the crystal and has multiple internal faces. A mount is configured to hold the crystal in a fixed location relative to a source of an X-ray beam and to shift the crystal automatically between two predefined dispositions: a first disposition in which the X-ray beam passes through the channel while diffracting from one or more of the internal faces, and a second disposition in which the X-ray beam passes through the channel without diffraction by the crystal.

In some embodiments, the mount is configured to shift the crystal between the two predefined dispositions by rotating the crystal about an axis, which may coincide with an endpoint of the channel. In a disclosed embodiment, the device includes an automatically-controlled actuator, which is energized in order to rotate the crystal into one of the predefined dispositions, and a return spring, which is configured to return the crystal to the other of the predefined dispositions when the actuator is released. Typically, the actuator is energized in order to rotate the crystal into the second disposition, and the device includes a stop, which engages the mount in the first disposition and is adjustable so as to fix an angle of entry of the X-ray beam into the channel.

In some embodiments, the device includes at least one X-ray mirror, which is configured to collect X-rays emitted from the source so as to generate and direct the X-ray beam into the channel of the crystal. In one embodiment, the at least one X-ray mirror, includes a first X-ray mirror, which is positioned so as to intercept the X-rays emitted from the source at a first angle so as to direct a first beam into the channel of the crystal, and a second X-ray mirror, which is positioned so as to intercept the X-rays emitted from the source at a second angle, different from the first angle, so as to direct a second beam toward a target while bypassing the channel. The first and second X-ray mirrors may be operative to intercept the X-rays so as to generate the first and second beams simultaneously, and the device may include an exit aperture, which is automatically positionable so as to permit either the first beam, after transit of the channel, or the second beam to exit the device, while blocking the other of the first and second beams.

There is also provided, in accordance with an embodiment of the present invention, an X-ray optical device, which includes first and second X-ray mirrors, which are respectively positioned so as to intercept X-rays emitted from a source at different, respective first and second angles, and are configured to generate and direct respective first and second X-ray beams toward a target along different, respective first and second axes. An exit aperture is positionable automatically so as to permit the X-rays to exit the device along either of the first and second axes, while blocking the other of the first and second axes.

In a disclosed embodiment, the exit aperture includes a slit, which is translatable in a direction transverse to the axes. Additionally or alternatively, the first and second X-ray mirrors each include a curved substrate with a multilayer coating.

There is additionally provided, in accordance with an embodiment of the present invention, X-ray optical apparatus, which includes an X-ray mirror, which is configured to collect X-rays emitted from a source so as to generate an X-ray beam. First and second rotatable mounts hold respective first and second X-ray optical components configured to intercept and condition the X-ray beam. An exit aperture is positionable so as to select a beam axis along which X-rays are to exit the apparatus toward a target. A processor is coupled to automatically control rotation of the rotatable mounts and positioning of the exit aperture.

In one embodiment, the X-ray mirror is configured to direct a first X-ray beam along a first axis, and the first X-ray optical component includes a further mirror configured to direct a second X-ray beam along a second axis.

In another embodiment, the first and second X-ray optical components respectively include first and second crystals, each containing a respective channel, which passes through the crystal and has multiple internal faces. Typically, the mounts are configured to rotate each of the crystals between a first disposition in which the X-ray beam passes through the channel while diffracting from one or more of the internal faces, and a second disposition in which the X-ray beam passes through the channel without diffraction by the crystal.

There is further provided, in accordance with an embodiment of the present invention, a method for conditioning an X-ray beam, which includes positioning a crystal containing a channel, which passes through the crystal and has multiple internal faces, so that the X-ray beam enters the channel. The crystal is shifted automatically between two predefined dispositions: a first disposition in which the X-ray beam passes through the channel while diffracting from one or more of the internal faces, and a second disposition in which the X-ray beam passes through the channel without diffraction by the crystal.

There is moreover provided, in accordance with an embodiment of the present invention, a method for generating an X-ray beam, which includes automatically positioning first and second X-ray mirrors to intercept X-rays emitted from a source at different, respective first and second angles so as to generate and direct respective first and second X-ray beams toward a target along different, respective first and second axes. An exit aperture is automatically positioned so as to permit the X-rays to exit the device along either of the first and second axes, while blocking the other of the first and second axes.

The present invention will be more fully understood from the following detailed description of the embodiments thereof, taken together with the drawings in which:

DETAILED DESCRIPTION OF EMBODIMENTS

Figure 1:
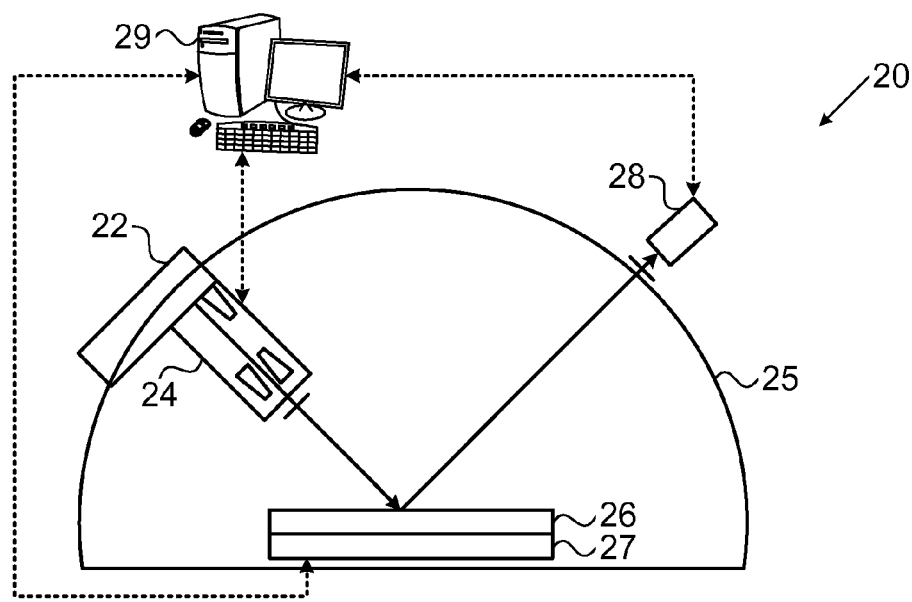
FIG. 1 is a schematic side view of a system for X-ray analysis, in accordance with an embodiment of the present invention.

As explained above in the Background section, different sorts of X-ray measurements typically require different beam characteristics, which in turn entail the use of different optical components and configurations. Although some X-ray instruments that are known in the art permit fast exchange of pre-aligned optical components, known designs do not fully address the risks of a user dropping (and thus damaging) or misaligning the optical components, which are typically delicate and expensive. Furthermore certain environments, such as the clean room of a highly automated semiconductor manufacturing facility, are not at all conducive to manual exchange of optics by a user.

Embodiments of the present invention that are described hereinbelow provide X-ray optics, beam conditioning devices and methods that enable the user of an X-ray analytical system to conveniently change parameters of the X-ray beam safely and precisely under automated control. The variable parameters may include the degree of collimation, monochromaticity, and spatial extent. As a result, the same X-ray source and beam conditioning device can be used in multiple different measurement applications without requiring the user to exchange optical components or perform manual alignment when switching between different types of measurements.

For example, in some embodiments the beam is conditioned so as to enable X-ray diffraction (XRD) measurements to be made from polycrystalline samples. These embodiments typically require a high-flux beam with only modest collimation. Depending on the type of measurement, the desired beam may be convergent (focusing) or divergent or modestly collimated to within about 0.1-0.2°. The requirements for monochromaticity are also often not too stringent and can be satisfied by Ka1 and Ka2 spectral components that are produced by an X-ray tube comprising a metal anode, such as Cu, Cr or Mo. It may be desirable, however, to remove higher-energy components such as the Kb line. In these embodiments, the beam conditioning device may apply a multilayer mirror, either curved or flat (such as those mentioned above in the Background section) in order to provide the desired output beam properties.

In other embodiments, the beam may be used in measuring X-ray reflectivity (XRR) from samples of various sorts of materials (such as amorphous, polycrystalline or single crystal materials). In these embodiments, the required beam properties depend on the thickness of the layers that are to be analyzed. For very thin layers, less than 10 nm thick, the collimation and monochromatization requirements are only modest, and a multilayer mirror can be used to provide a beam with 0.1-0.2° divergence containing Ka1 and Ka2 components with Kb largely removed. For thicker films, the beam conditioning requirements are more stringent, and crystal optics, such as a channel-cut crystal, can be used to reduce the divergence of the beam to a few millidegrees and remove all but the Ka1 wavelength component.

For high-resolution X-ray diffraction (HRXRD) measurements from single-crystal materials, such as semiconductor wafers (made from Si or alloys such as SiGe and Si:C, as well as compound semiconductors such as GaAs, InP, GaN and their alloys), beam conditioning requirements are much more stringent. In these embodiments, a beam conditioning device in accordance with an embodiment of the present invention may apply crystal optics to achieve a divergence of only a few millidegrees and a spectral width that includes only a fraction of the Ka1 line. The sort of channel-cut crystals described above in the Background section may be applied in this case.

In some embodiments, the beam conditioning device automatically adjusts the spatial extent of the beam in order to give an optimal signal from a sample. For example, an adjustable aperture, such as a motorized slit, may be used to restrict the beam. This sort of restriction is useful particularly if the unrestricted beam has a size on the sample (footprint) that is larger than the desired measurement area (possibly due to geometric factors such as low incidence angle). Additionally or alternatively, the aperture may be used to select a beam among multiple beams with different properties that are generated simultaneously in the beam conditioning device.

FIG. 1 is a schematic side view of a system 20 for X-ray analysis of a sample 26, in accordance with an embodiment of the present invention. An X-ray source 22, such as an X-ray tube, generates X-rays due to impact of high-energy electrons on a metal target (anode), such as Cu, Cr or Mo. The beam emitted by the X-ray source 22 is typically divergent and polychromatic. A beam conditioning device 24 applies X-ray optics to generate an output beam with properties that are suitable for the desired type of analysis of sample 26, as described in greater detail hereinbelow.

Sample 26 is typically mounted in a chamber 25 on a motorized stage 27, which can be controlled automatically to provide translational and rotational motion of the sample with respect to the incident X-ray beam. The elevation angle ($\omega$) of the X-ray beam, measured with respect to the surface of the sample 26 can be adjusted by either rotating X-ray source 22 and beam conditioning device 24 or by rotating sample 26, using motorized stage 27, with respect to a fixed incident beam. A suitable processor 29, such as a computer with appropriate input and output connections, serves as an automated controller of the operation of system 20, including the rotation and translation of motorized stage 27 and the configuration of beam conditioning device 24, as explained below.

X-rays scattered from sample 26 are measured at a certain angle or over a range of angles with respect to the incident beam. In X-ray diffraction measurements, this angle is referred to as the 2θ angle, and it is adjusted under control of processor 29. The scattered X-rays may pass through one or more analyzing optical components such as slits, crystals or mirrors (not shown in the figures), depending on the sample under analysis, and are then sensed by a detector 28. The optimal detector type may be selected depending on the measurement being made, as is known in the art. The electrical signal from detector 28 is pre-processed and fed into processor 29 for analysis.

Figure 2:
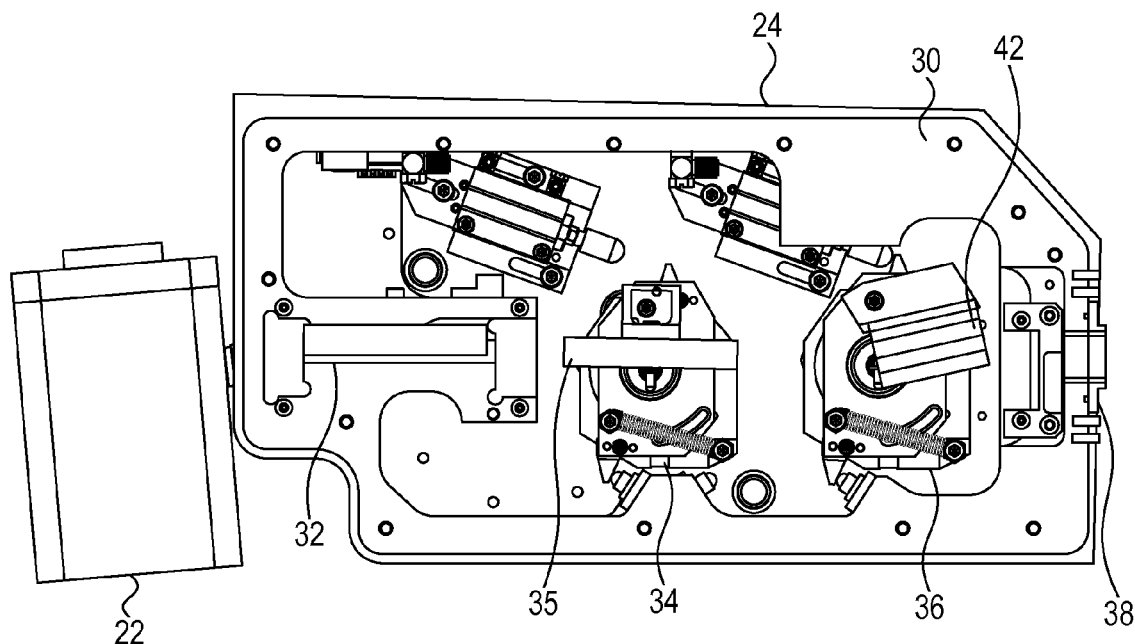
FIG. 2 is a schematic side view of an X-ray beam conditioning device, in accordance with an embodiment of the present invention.

FIG. 2 is a schematic side view of beam conditioning device 24, in accordance with an embodiment of the present invention. Beam conditioning device 24 comprises a housing 30, which contains a set of X-ray optical components that are configurable under automated control, by processor 29, for example, in order to vary and adjust the properties of the X-ray beam that is incident on sample 26. FIG. 2 shows one particular configuration of these components by way of example, and some representative alternative configurations are shown in the figures that follow. It will be apparent to those skilled in the art, however, that the principles of this embodiment may be applied in other beam conditioning configurations, as well, which are all considered to be within the scope of the present invention.

Beam conditioning device 24 comprises an X-ray mirror 32, which collects and collimates the X-rays emitted from X-ray source 22. Typically, X-ray mirror 32 is mounted so as to be stationary within housing 30 and comprises a multilayer optic, which may be flat or curved.

Figure 6A:
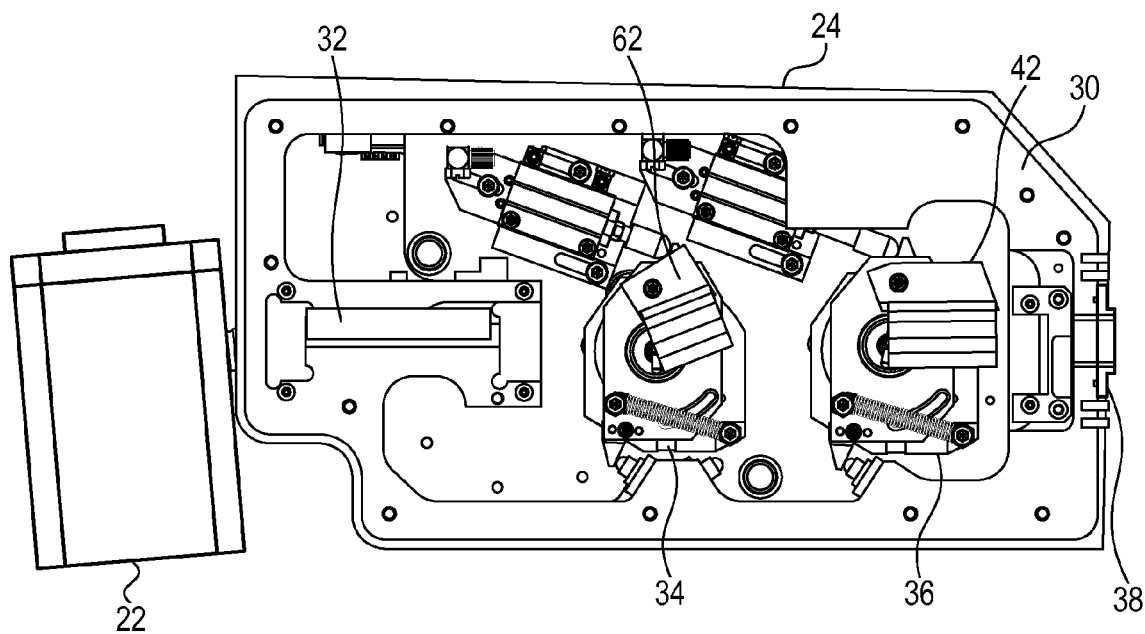
FIGS. 6A and 6B are schematic side views of an X-ray beam conditioning device in two different operational configurations, in accordance with an alternative embodiment of the present invention.
Figure 6B:
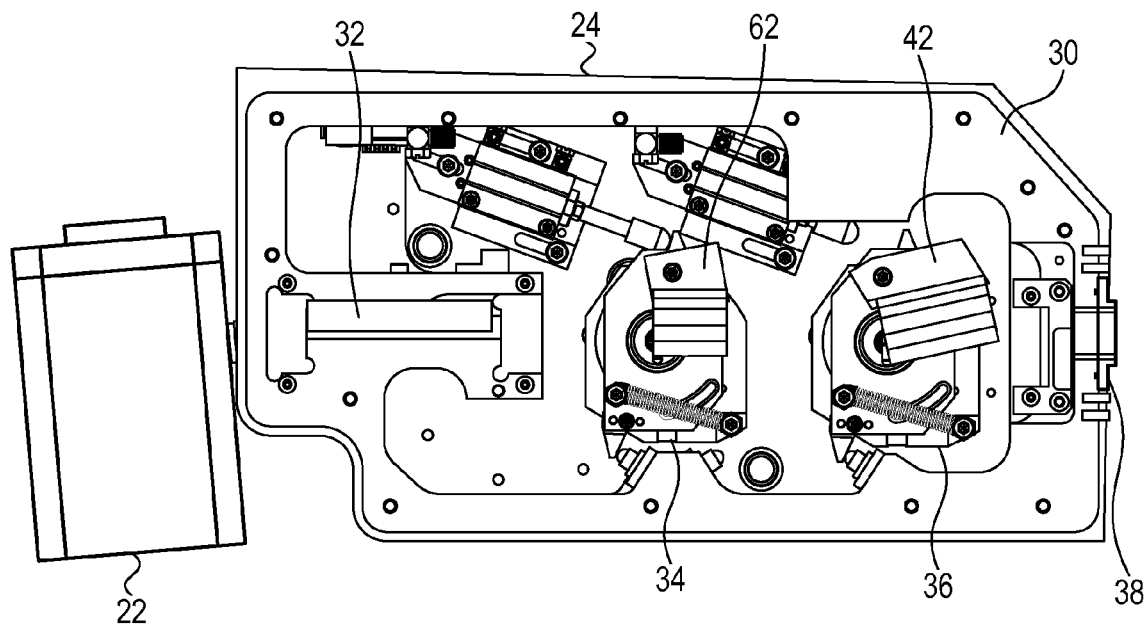

In addition to X-ray mirror 32, beam conditioning device 24 comprises two mounts 34 and 36, which hold respective X-ray optical components that can be used to intercept and condition the X-ray beam. In the embodiment shown in FIG. 2, mount 34 holds a second X-ray mirror 35, while mount 36 holds a channel-cut crystal 42. Typically, second X-ray mirror 35 generates a collimated X-ray beam along a different axis and having different beam properties from the collimated beam generated by X-ray mirror 32. Alternatively, either or both of mounts 34 and 36 may hold optics of other types. (For example, mount 34 may hold a second channel-cut crystal, as shown in FIGS. 6A and 6B.) Typically, mounts 34 and 36 are rotatable, as illustrated in FIGS. 3A and 3B, so as to change the angle at which the X-rays are incident on the corresponding optical components.

Figure 4A:
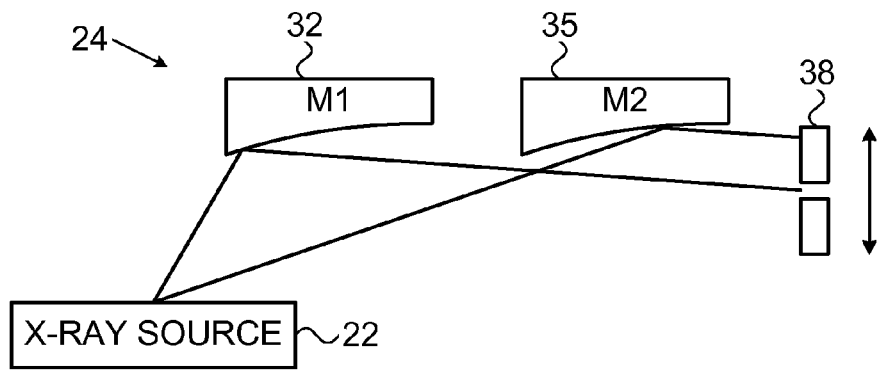
FIGS. 4A and 4B are schematic side views showing elements of an X-ray beam conditioning device with a movable aperture in two different operational configurations, in accordance with an embodiment of the present invention.

At the exit from housing 30, beam conditioning device 24 comprises an exit aperture 38, which is positionable so as to select the beam axis along which X-rays are to exit the beam conditioning device 24 toward the target location on sample. This beam selection function is illustrated in FIGS. 4A/B and in FIG. 5. Typically, exit aperture 38 comprises one or more motorized slits, which may additionally or alternatively be operated to control the spatial extent of the exiting beam.

Figure 3A:
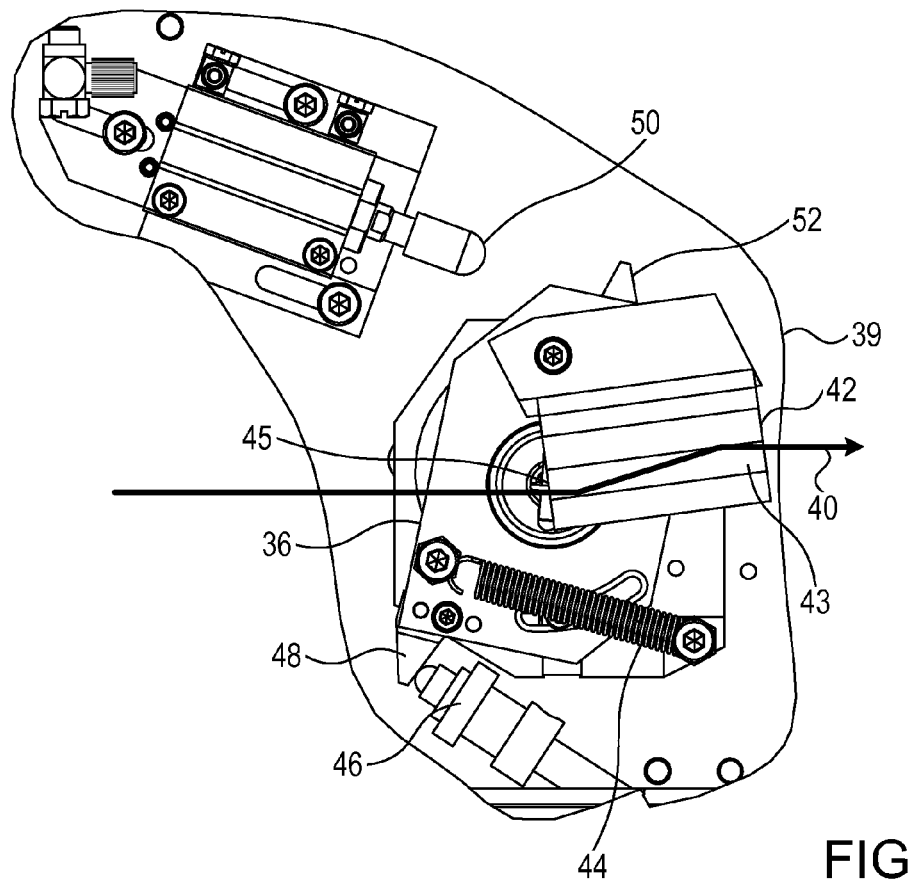
FIGS. 3A and 3B are schematic side views of a crystal assembly for X-ray beam conditioning in two different operational configurations, in accordance with an embodiment of the present invention.
Figure 3B:
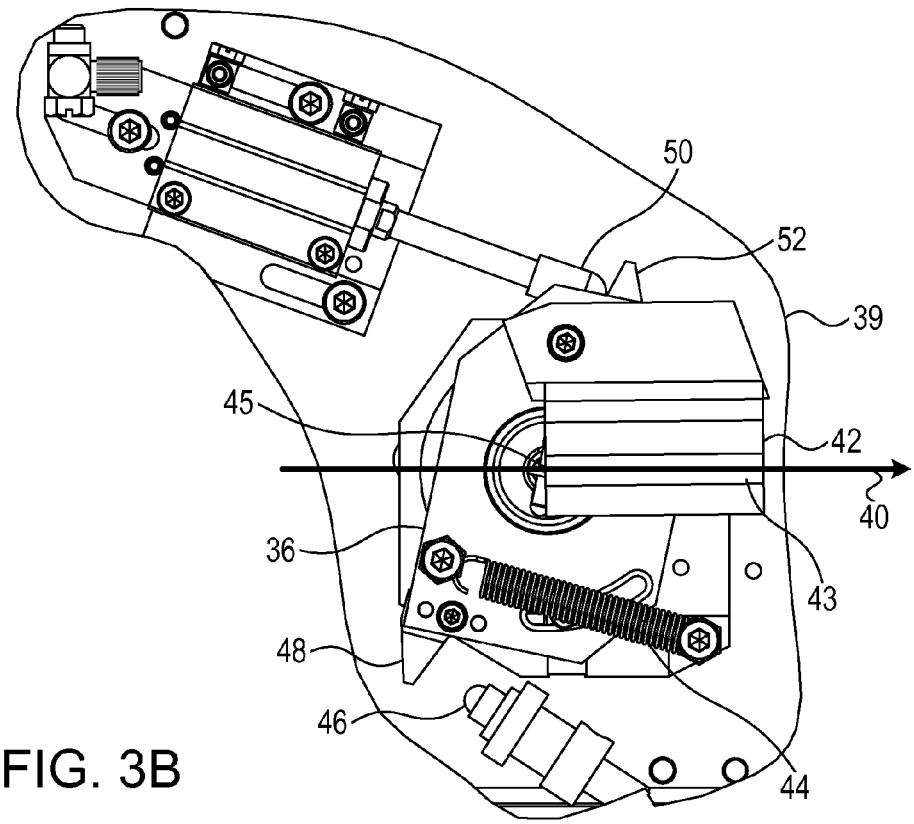

FIGS. 3A and 3B are schematic side views of a crystal assembly 39 for X-ray beam conditioning in two different operational configurations, in accordance with an embodiment of the present invention. Crystal assembly 39, which is a part of beam conditioning device 24, contains rotatable mount 36 with channel-cut crystal 42, as shown in FIG. 2. Channel-cut crystal 42 contains a channel 43, which passes through the channel-cut crystal 42 and has multiple internal faces. Mount 36 holds the channel-cut crystal 42 in a fixed location within housing and shifts the channel-cut crystal 42 between two predefined dispositions:

The disposition of FIG. 3A, in which an X-ray beam 40 passes through channel 43 while diffracting from one or more of the internal faces; and The disposition of FIG. 3B, in which X-ray beam 40 passes through channel 43 without diffraction by channel-cut crystal 42.

Typically, the input beam to channel 43 is already at least partly collimated, for example by X-ray mirror or second X-ray mirror 35, which is positioned to receive the X-ray beam 40 from X-ray source 22 and to direct the X-ray beam 40 into the channel 43. The disposition of FIG. 3A provides an output X-ray beam 40 with enhanced collimation and narrower spectral width, as the result of diffraction from the internal faces of the channel 43. These enhancements of the beam quality come at the expense of lower beam flux. The disposition of FIG. 3B enables X-ray beam 40 to pass through channel 43 directly without substantially reducing the beam flux.

As noted earlier, mount 36 shifts channel-cut crystal 42 between its two predefined dispositions by rotating the channel-cut crystal 42 about an axis, which coincides with an endpoint 45 of channel 43. In the pictured example, the endpoint 45 is the point of entry of X-ray beam 40 into channel 43, but the endpoint 45 may alternatively be the point of exit. An actuator 50 is energized in order to rotate the channel-cut crystal 42 into one of the predefined dispositions—in this case the "pass-through" disposition of FIG. 3B—by engaging a corresponding protrusion 52 of mount 36. A return spring returns the channel-cut crystal 42 to the other disposition (that of FIG. 3A) when actuator 50 is released. In this latter disposition, a stop 46 engages a detent 48 on mount 36 to hold the mount 36 at the desired angle. Stop 46 may be adjustable so as to fix precisely the angle of entry of X-ray beam 40 into channel 43.

Actuator 50 may be energized pneumatically, for example, or by a solenoid or motor or any other suitable means known in the art. In the pass-through disposition of FIG. 3B, the positioning accuracy requirements are not stringent, since channel 43 simply has to be angled sufficiently to allow X-ray beam 40 to pass through without being blocked by the channel 43. On the other hand, the disposition of FIG. 3A may require angular accuracy and repeatability to with a few seconds of arc to provide the required beam characteristics. The desired accuracy is maintained by suitable pre-hardening of stop 46 and detent 48 to ensure a repeatable hardware location. As noted earlier, stop 46 may be adjustable to enable precise initial set-up, but once adjusted, the construction of mount 36 is accurate enough to enable subsequent switching between dispositions without further alignment. Optionally, stop 46 can be precision-motorized for fine adjustment to allow use of the channel-cut crystal 42 for different mirrors.

Although FIGS. 3A and 3B show a particular mechanical design and configuration that can be used to achieve the desired shift between the two dispositions of channel-cut crystal 42, alternative designs for this purpose will be apparent to those skilled in the art after reading the present description and are considered to be within the scope of the present invention.

Figure 4B:
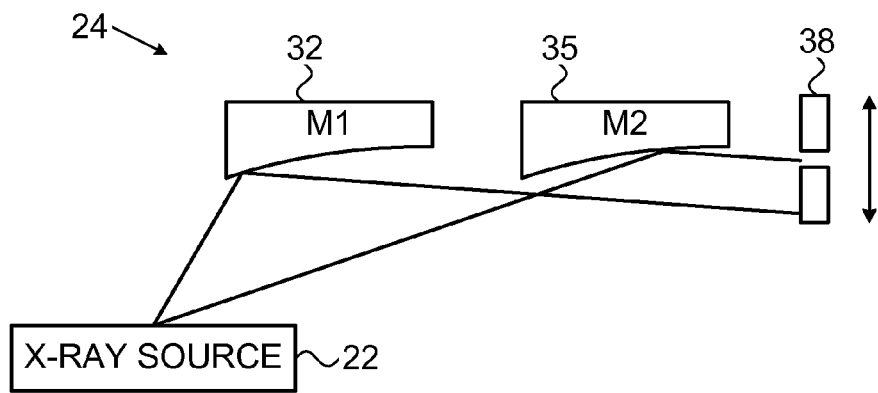

FIGS. 4A and 4B are schematic side views showing elements of X-ray beam conditioning device 24 in two different operational configurations, in accordance with another embodiment of the present invention. This embodiment illustrates the ability of the beam conditioning device 24 to switch its output beam between X-ray mirrors 32 and 35. As will be shown in FIG. 5, this mirror switching may be combined with the crystal switching described above.

X-ray source 22 emits X-rays over a wide range of angles, thus enabling X-ray mirrors 32 and 35 to be placed so as to intercept different rays from the X-ray source 22 at different angles. Each of the X-ray mirrors 32 and 35 in the present example comprises a curved substrate with a multilayer coating, and thus collects, collimates and directs the intercepted rays toward sample 26 along a different, respective beam axis. Exit aperture 38 is shifted automatically, for example by processor 29, between the positions of FIG. 4A and FIG. 4B in order to permit the collimated beam to exit the beam conditioning device 24 along one of these axes, while blocking the other axis. Thus, the exit aperture 38 blocks the beam that is not required for the purpose at hand, so that only the required beam is allowed to exit from beam conditioning device 24 toward sample 26. As noted earlier, exit aperture 38 may comprise a slit, which is driven either by an actuator, a motor or another suitable mechanical drive to translate in a direction transverse to the axes of the beams from X-ray mirrors 32 and 35.

Figure 5:
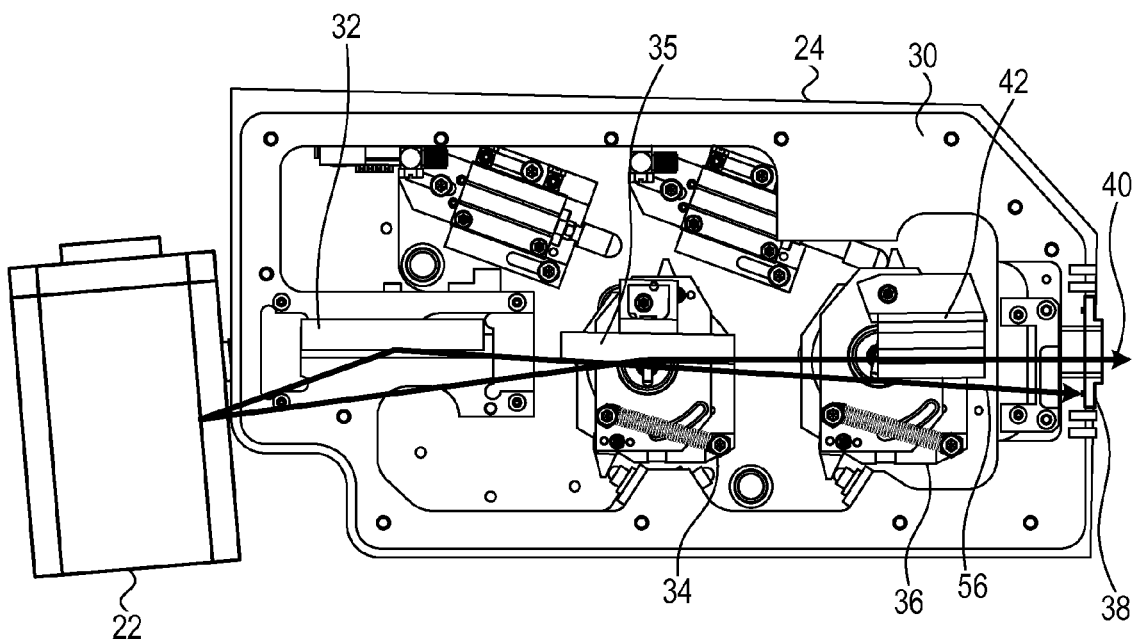
FIG. 5 is a schematic side view of an X-ray beam conditioning device, in accordance with an embodiment of the present invention.

FIG. 5 is a schematic side view of X-ray beam conditioning device 24, in accordance with an embodiment of the present invention that illustrates the principles shown in FIGS. 4A/B. Here the second X-ray mirror 35 intercepts the X-rays emitted from X-ray source 22 at a certain angle and directs collimated X-ray beam 40 into the channel 43 of channel-cut crystal 42. (The channel-cut crystal 42 in this figure is disposed in the pass-through configuration of FIG. 3B, but could be turned by mount 36 to the diffracting configuration of FIG. 3A.) X-ray mirror 32 intercepts the X-rays from X-ray source 22 at a different angle, and directs a second collimated X-ray beam 56 toward the exit aperture 38 from beam conditioning device 24 while bypassing the channel 43 through channel-cut crystal 42. As explained above, X-ray mirrors 32 and 35 intercept and collimate the X-ray beam 40 simultaneously. Exit aperture 38 is positioned in FIG. 5 so as to permit X-ray beam 40 to exit from beam conditioning device 24, after transit of the channel 43 in channel-cut crystal 42, while blocking the second collimated X-ray beam 56. Alternatively, the exit aperture 38 may be shifted to pass the second collimated X-ray beam 56 and block X-ray beam 40.

FIGS. 6A and 6B are schematic side views of X-ray beam conditioning device 24 in two different operational configurations, in accordance with an alternative embodiment of the present invention. In this embodiment, mount 34 holds a second channel-cut crystal 62, rather than a mirror as in the preceding embodiments, and is operative to rotate the second channel-cut crystal 62 between diffracting and pass-through configurations in the same manner as channel-cut crystal 42 in mount 36. Thus, processor 29 may control the beam conditioning device 24 to generate output beams with desired spectral properties and collimation by rotating the second channel-cut crystal 62 to the diffractive disposition while the channel-cut crystal 42 is in the pass-through disposition (FIG. 6A), or vice versa (FIG. 6B). In alternative configurations (not shown in the figures), the channel-cut crystal 42 and the second channel-cut crystal 62 may be disposed to diffract the X-ray beam 40, or both may be disposed to pass the X-ray beam 40 from X-ray mirror 32. Exit aperture 38 is typically adjusted in accordance with the configuration of the the channel-cut crystal 42 and the second channel-cut crystal 62.

Although the pictured embodiments show certain particular arrangements of X-ray optical components in beam conditioning device 24, the principles of the present invention may likewise be applied in making other optical arrangements for similar purposes (possibly comprising a smaller or greater number of distinct components). It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An X-ray optical device, comprising:
   a crystal containing a channel, which passes through the crystal and has multiple internal faces;
   a mount, which is configured to hold the crystal in a fixed location relative to a source of an X-ray beam and to shift the crystal automatically between two predefined dispositions by rotating the crystal about an axis:
   a first disposition in which the X-ray beam passes through the channel while diffracting from one or more of the multiple internal faces; and
   a second disposition in which the X-ray beam passes through the channel without diffraction by the crystal;
   an automatically-controlled actuator, which is energized in order to rotate the crystal about the axis into one of the two predefined dispositions, wherein the automatically-controlled actuator is energized in order to rotate the crystal into the second disposition; and
   a stop, which engages the mount in the first disposition and is adjustable so as to fix an angle of entry of the X-ray beam into the channel.

2. The X-ray optical device according to claim 1, wherein the axis coincides with an endpoint of the channel.

3. The X-ray optical device according to claim 1, further comprising a return spring, which is configured to return the crystal to the other of the two predefined dispositions when the actuator is released.

4. The X-ray optical device according to claim 1, and comprising at least one X-ray mirror, which is configured to collect X-rays emitted from the source so as to generate and direct the X-ray beam into the channel of the crystal.

5. An X-ray optical device, comprising:
   a crystal containing a channel, which passes through the crystal and has multiple internal faces;

a mount, which is configured to hold the crystal in a fixed location relative to a source of an X-ray beam and to shift the crystal automatically between two predefined dispositions:
- a first disposition in which the X-ray beam passes through the channel while diffracting from one or more of the multiple internal faces; and
- a second disposition in which the X-ray beam passes through the channel without diffraction by the crystal; and at least one X-ray mirror, which is configured to collect X-rays emitted from the source so as to generate and direct the X-ray beam into the channel of the crystal, wherein the at least one X-ray mirror comprises:
- a first X-ray mirror, which is positioned so as to intercept the X-rays emitted from the source at a first angle so as to direct a first beam into the channel of the crystal; and
- a second X-ray mirror, which is positioned so as to intercept the X-rays emitted from the source at a second angle, different from the first angle, so as to direct a second beam toward a target while bypassing the channel.

6. The X-ray optical device according to claim 5, wherein the first and second X-ray mirrors are operative to intercept the X-rays so as to generate the first and second beams simultaneously, and wherein the X-ray optical device comprises an exit aperture, which is automatically positionable so as to permit either the first beam, after transit of the channel, or the second beam to exit the X-ray optical device, while blocking the other of the first and second beams.

7. A method for conditioning an X-ray beam, comprising:
positioning a crystal containing a channel, which passes through the crystal and has multiple internal faces, so that the X-ray beam enters the channel; and
shifting the crystal automatically between two predefined dispositions by rotating the crystal about an axis by an automatically-controlled actuator, which is energized in order to rotate the crystal about the axis into one of the two redefined dispositions, while a return spring returns the crystal to the other of the two predefined dispositions when the automatically-controlled actuator is released, the two predefined dispositions comprising:
- a first disposition in which the x-ray beam passes through the channel while diffracting from one or more of the multiple internal faces; and
- a second disposition in which the X-ray beam passes through the channel without diffraction by the crystal.

8. The method according to claim 7, wherein the axis coincides with an endpoint of the channel.

9. The method according to claim 7, further comprising applying an X-ray mirror to collect X-rays emitted from a source so as to generate and direct the X-ray beam into the channel of the crystal.

* * * * *